United States Patent [19]

Kaplan et al.

[11] 4,035,381

[45] July 12, 1977

[54] ANTIBACTERIAL AGENTS

[75] Inventors: Murray Arthur Kaplan, Syracuse; William Joseph Gottstein, Fayetteville; Alphonse P. Granatek, Baldwinsville, all of N.Y.

[73] Assignee: Bristol-Myers Company, New York, N.Y.

[21] Appl. No.: 735,552

[22] Filed: Oct. 26, 1976

[51] Int. Cl.$^2$ .................................... C07D 499/80
[52] U.S. Cl. ..................... 260/306.7 C; 424/271
[58] Field of Search ................. 260/306.7 C, 239.1

[56] References Cited

U.S. PATENT DOCUMENTS 3,198,804   8/1965   Johnson et al. ............ 260/306.7 C

FOREIGN PATENT DOCUMENTS 1,436,959   5/1976   United Kingdom ............ 260/239.1

Primary Examiner—Gerald A. Schwartz
Attorney, Agent, or Firm—David M. Morse

[57] ABSTRACT

The alkali metal salts of the reaction products of ampicillin or amoxicillin with 5-formyl-2-furansulfonic acid are found to be stable, useful water-soluble forms of the penicillin antibiotics especially advantageous for parenteral administration.

7 Claims, No Drawings

ANTIBACTERIAL AGENTS

BACKGROUND OF THE INVENTION

1. Field of the Invention

The penicillin derivatives of the present invention possess in general the usual attributes of that family of antibacterial agents and are particularly useful in the treatment of bacterial infections by both oral and parenteral administration.

2. Description of the Prior Art

The semi-synthetic penicillins D(-)-α-aminobenzylpenicillin (ampicillin) and D(-)-α-amino-p-hydroxybenzylpenicillin (amoxicillin) are disclosed in U.S. Pat. Nos. 2,985,648 (ampicillin) and 3,674,776 (amoxicillin). While these penicillins possess a broad spectrum of antibacterial activity and can be administered both orally and parenterally, problems have been encountered in obtaining dosage forms suitable for intravenous administration. Thus, the only form of ampicillin generally available for intravenous injection has been the water-soluble sodium salt. The aqueous solution of this salt, however, has an extremely short shelf-life (about one hour at room temperature when reconstituted at 250 mg./ml.) and the solution is somewhat irritating on injection, presumably due to its high pH. In addition, the sodium salt of ampicillin is hygroscopic and cannot be prepared by lyophilization. With respect to amoxicillin, no parenteral dosage form of this antibiotic is presently being marketed. A crystalline sodium salt of amoxicillin has not yet been made and the crystalline potassium salt can be made only with great difficulty, e.g. preparation by lyophilization is not possible. The potassium salt, moreover, when reconstituted with water to a concentration of 250 mg./ml., is stable for only 15 minutes at room temperature and precipitates out of solution on standing.

Various aldehyde and ketone condensation products of α-aminopenicillins including ampicillin and amoxicillin have been disclosed in the patent and scientific literature. Thus, for example, derivatives of various α-aminopenicillins with nitro-substituted heterocyclic aldehydes are disclosed in U.S. Pat. No. 3,647,781. Condensation products of ampicillin or ring-substituted ampicillins with aromatic heterocyclic aldehydes are disclosed in U.K. Pat. No. 1,436,959. Other patent publications disclosing derivatives of α-aminopenicillins with aldehydes or ketones include U.S. Pat. Nos. 3,198,804 and 3,558,602 (various aldehydes and ketones), U.S. Pat. No 3,198,788 and South African Pat. No. 72/8475 (formaldehyde), U.S. Pat. No. 3,230,214 (aromatic or heteroaromatic aldehydes containing an ortho hydroxyl substituent), U.S. Pat. No. 3,325,479 (diketones), U.S. Pat. Nos. 3,489,746, 3,549,746, 3,814,800 and U.K. Pat. No. 1,224,619 (acetone), U.S. Pat. No. 3,725,389 (N-substituted-4-piperidones), U.S. Pat. NO. 3,888,848 (chloral hydrate), U.S. Pat. No. No. (various aldehydes) and South African Pat. No. 72/8474 (acetaldehyde). While certain of these derivatives, e.g. hetacillin, the acetone adduct of amplicillin, are disclosed as being somewhat more stable in aqueous solution as sodium salts than the parent penicillins, it would be a substantial advantage to the physician if reconstituted solutions of ampicillin and amoxicillin (or derivatives of these penicillins which completely and rapidly hydrolyze in aqueous solution to form ampicillin and amoxicillin) were stable for longer periods of time.

It is, accordingly, an object of the present invention to provide new water-soluble forms of ampicillin and amoxicillin which can be administered both orally and parenterally (including intravenous administration) and which do not have the disadvantages associated with the known intravenous forms of these penicillins, i.e. the alkali metal salts. In particular, it is an object of the present invention to provide new derivatives of ampicillin and amoxicillin which (1) upon the addition of water will give true solutions of ampicillin or amoxicillin suitable for both oral and parenteral administration, (2) have acceptable thermal stability in the solid state, (3) in aqueous solution at a concentration of about 250 mg./ml. have a useful life of at least several hours at room temperature, (4) result in reduced irritation on parenteral administration and (5) can be readily and simply prepared by lyophilization as well as by solvent precipitation methods. These and other objects of the present invention will be apparent from the followijng description.

SUMMARY OF THE INVENTION

The present invention provides novel water-soluble pharmaceutically acceptable forms of the antibiotics D(-)-α-aminobenzylpenicillin (ampicillin) and D(-)-α-amino-p-hydroxybenzylpenicillin (amoxicillin) having the formula

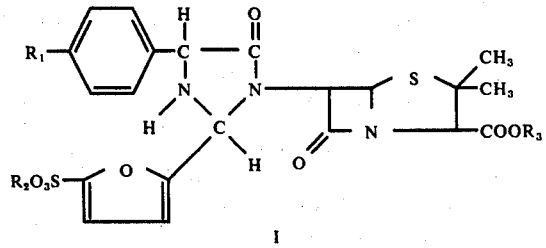

I wherein $R_1$ is hydrogen or hydroxyl and $R_2$ and $R_3$ are alike or different and are each sodium or potassium. In the preferred embodiment, $R_2$ and $R_3$ in the above formula are both sodium. In the body or in dilute aqueous solution or acidic aqueous solution at any concentration, the alkali metal salts of the present invention rapidly hydrolyze to the parent α-amino penicillins.

DETAILED DESCRIPTION

The alkali metal salts of formula I may be prepared by a process which comprises 1. treating an aqueous suspension of ampicillin or amoxicillin or a hydrate thereof, preferably the trihydrate form thereof, with 5-formyl-2-furansulfonic acid or a sodium or potassium salt thereof and sufficient watersoluble sodium or potassium base to raise the pH of the reaction mixture to between about 5.5 and 8 and preferably pH 6.2–7.2 and to form in solution the desired compound of formula I; and 2. recovering from the solution said compound.

The compounds of formula I have an asymmetric center as indicated by the structural formula. Thus, compounds of formula I may exist in the form of the DL mixture or as the individual D or L isomers. The compounds may have the cyclic structure shown in formula I or the open (Schiff's base) structure represented by the formula

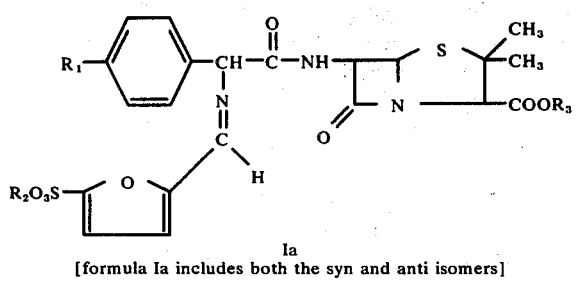

Ia

[formula Ia includes both the syn and anti isomers]

wherein $R_1$, $R_2$ and $R_3$ are as defined above. Compounds of both the Schiff's base and cyclic structure are intended to be included within the scope of the present invention. Formula I, therefore, as used herein and in the claims encompasses both the cyclic and Schiff's base forms of the aldehyde condensation products provided by the present invention.

The starting material α-aminopenicillin used in the above process may be any known form of ampicillin or amoxicillin including both the anhydrous and hydrated forms. The preferred starting materials are ampicillin trihydrate or amoxicillin trihydrate. The concentration of ampicillin or amoxicillin is not critical, and good results have been obtained with concentrations between about 25–300 milligrams α-aminopenicillin per milliliter of solvent. The starting material penicillin is preferably ground and screened to a finely divided state, e.g. less than 200 mesh, so as to increase the surface area and rate of reaction.

The α-aminopenicillin is slurried in water to form an aqueous suspension. An alternative to using an aqueous suspension in step (1) would be to suspend the α-aminopenicillin starting material in an organic solvent which is (1) a solvent for the alkali metal salt end-product, (2) miscible with the aldehyde, (3) chemically inert toward the penicillin starting material and end-product and (4) easily removable from the end-product as by mild drying. Examples of organic solvents which might be employed are dimethylsulfoxide and dimethylformamide. Because of the difficulty of removing residual organic solvent from the alkali metal salt end-product, however, the starting material is preferably employed as an aqueous suspension.

After obtaining the α-aminopenicillin starting material in suspension, the desired alkali metal salt of formula I is formed in solution by addition of the aldehyde, preferably in the form of its sodium or potassium salt, and an amount of water-soluble sodium or potassium base sufficient to raise the pH of the reaction mixture to between about 5.5 and 8. As the pH is raised to within this range the alkali metal salt of the reaction product of ampicillin or amoxicillin and 5-formyl-2-furansulfonic acid is formed and goes into solution.

The temperature at which step (1) is carried out is not critical. The reaction may be performed at room temperature, but higher or lower temperatures may be used. The preferred temperature range is about 40°–45° C.

About one mole of the aldehyde is preferably added per mole of α-aminopenicillin starting material, but some reaction will take place no matter what molar proportion of the reactants is used.

The alkali metal base may be any water soluble base capable of (1) providing sodium or potassium ions and (2) raising the pH of the reaction mixture to between about 5.5 and 8, most preferably 6.2 to 7.2. Preferred bases because of their desirable solubility properties are sodium or potassium hydroxide. Preferably the base is added in the form of an aqueous solution and is added slowly to the reaction mixture with stirring until the reaction is shown to be complete by pH measurement and by formation of a solution or near solution.

For best results the solution obtained at the conclusion of Step (1) is filtered to remove solid impurities prior to the recovery Step (2). Before filtration, the solution may optionally be carbon-treated with activated carbon to assist in removal of any colored impurities.

The desired product of formula I is then recovered from aqueous or non-aqueous solution as by precipitation or lyophilization. Precipitation of the alkali metal salt may be effected by addition of an organic solvent in which the desired salt is insoluble, i.e. an antisolvent. Examples of such antisolvents include isopropanol, n-propanol, ethanol, t-butanol and acetonitrile. The solvent to be used in the precipitation step should be one which can be easily removed from the end-product under conditions which will not result in any significant decomposition of the alkali metal salt. The most preferred antisolvent may be added to the solution resulting from Step (1) or, alternatively and preferably, the solution containing the desired alkali metal salt is added with stirring to a large excess of the antisolvent. The alkali metal salt of formula I is then recovered by filtration, washed with a suitable organic solvent, e.g. isopropanol, and dried by conventional procedures, e.g. vacuum-drying at 50°–56° C. for 24–48 hours or air drying at 60° C. for 48 hours. As an alternative procedure to recovering the end-product by precipitation, the salt of formula I may also be recovered by lyophilization of the solution prepared in Step (1).

An alternative process for preparing the compounds of formula I comprises 1. forming a suspension of ampicillin or amoxicillin or a hydrate thereof in a suitable inert organic solvent, said solvent being a solvent for the triethylamine salt of the 5-formyl-2-furansulfonic acid reaction product of ampicillin or amoxicillin and a non-solvent for the alkali metal salt of formula I;
2. treating the suspension with 5-formyl-2-furansulfonic acid or a sodium or potassium salt thereof and sufficient triethylamine to form in solution the triethylamine salt of the aldehyde reaction product of ampicillin or amoxicillin; and
3. precipitating the desired alkali metal salt of formula I from the solution by adding a solvent-soluble sodium or potassium base.

The α-aminopenicillin starting material used in the above process may be any of the forms of ampicillin or amoxicillin mentioned in connection with the firstdescribed method. The preferred starting materials are ampicillin trihydrate and amoxicillin trihydrate. The concentration of starting material and particle size are not critical, but the preferred conditions are as described above in connection with the first process.

The starting material is slurried in an inert organic solvent which is a solvent for the triethylamine salt of the aldehyde reaction product of ampicillin or amoxicillin but which is an non-solvent for the desired alkali metal salt of formula I. The solvent selected for Step (1) should preferably be easily removable from the end-product under conditions which will not result in any appreciable decomposition of the end-product.

Appropriate solvents for Step (1) may be determined by simple test. The preferred solvent is methanol as it is readily available, relatively inexpensive and fulfills the solubility requirements mentioned above.

The suspension formed in Step (1) is then treated with the aldehyde, preferably with about one mole of aldehyde per mole of penicillin starting material, and sufficient triethylamine to form in solution the triethylamine salt of the reaction product of 5-formyl-2-furansulfonic acid and ampicillin or amoxicillin. The reaction mixture is preferably stirred for at least about 30 minutes to ensure complete reaction. The amount of triethylamine used is not critical but preferably about 1 mole is used per mole of α-aminopenicillin starting material. The reaction of Step (2) is conveniently done at room temperature but temperatures higher or lower than this may be selected with the expected decrease or increase, respectively, in reaction time.

After formation of a solution or near-solution in Step (2), the reaction mixture is preferably carbon-treated and filtered as in the first-mentioned process discussed above.

The desired alkali metal salt of formula I may then be recovered from the solution of Step (2) by addition of a solvent-soluble sodium or potassium salt. The preferred salts are sodium or potassium salts of organic acids having between about 2 and 18 carbon atoms, e.g. solvent-soluble salts of such acids as 2-ethylhexanoic, caproic, oleic, glycolic, propionic, acetic, etc. Preferred salts for the methanol solvent system are sodium or potassium 2-ethylhexanoate, most preferably solutions of these salts in a methanol-miscible organic solvent such as isopropanol. The most preferred alkali metal salts are solutions of sodium or potassium 2-ethylhexanoate in isopropanol. The alkali metal salt is added, preferably slowly and with stirring, in sufficient quantity so as to obtain the maximum amount of precipitate from the solution. After complete precipitation has been effected, the reaction mixture is stirred, preferably for at least about 1 hour, and then filtered. The precipitate is washed with an appropriate organic solvent, e.g. methanol, and dried by conventional procedures, e.g. vacuum-drying at 50°-56° C. for 24-48 hours or air drying at 60° C. for 48 hours.

The second process may also be carried out without use of the triethylamine in Step (2). In this modified procedure the suspension of ampicillin or amoxicillin or hydrate thereof is suspended in an inert organic solvent which is a non-solvent for the product of formula I and the suspension then treated with 5-formyl-2-furansulfonic acid or a sodium or potassium salt thereof, and a solvent-soluble sodium or potassium base, said base being added in an amount sufficient to raise the pH of the reaction mixture to between about 5.5 and 8. It is preferred to use as bases the sodium or potassium salts mentioned above as being preferred in the second process. In the modified process the α-aminopenicillin starting material goes into solution and the insoluble alkali metal salt then precipitates out almost instantaneously. Since a solution is not obtained upon completion of the reaction, the reaction mixture is preferably stirred and heated to about 45°-50° C. for a period of time of up to several hours to ensure maximum yields of end-product. The solid product is removed by filtration, washed and dried to give the desired salt of formula I.

The alkali metal salts of the present invention may be used to provide pharmaceutical formulations which in the body or in dilute aqueous solution or in acidic aqueous solution at any concentration rapidly hydrolyze to the parent ampicillin or amoxicillin. These formulations possess the desirable properties of (1) acceptable thermal stability in the solid state, (2) high solubility in water, (3) satisfactory aqueous stability when reconstituted, (4) little or no muscle or vein irritation upon parenteral adminstration and (5) ease of preparation by both lyophilization and solvent precipitation methods.

The sodium and potassium salts of formula I may be dissolved in water to form relatively concentrated solutions of at least 250 mg./ml. of activity. Reconstituted aqueous solutions of 250 mg./ml. of activity are stable at room temperature for at least 4 to 8 hours in the case of the amoxicillin derivative (disodium salt) and at least 24 hours for the ampicillin derivative (disodium salt). When diluted to a concentration of 10 to 20 mg./ml. of activity, the disodium amoxicillin derivative is stable at room temperature for at least 24 hours.

Activities and oral and intramuscular absorption of the compounds of formula I are substantially equivalent to those of the parent penicillins.

The compounds of the present invention may be used to provide both oral and parenteral (including intravenous) antibiotic preparations for treatment of infectious diseases in poultry and animals, including man, caused by many Gram-positive and Gram-negative bacteria. The compounds and pharmaceutical compositions containing a compound of formula I as active ingredient are also of value as nutritional supplements in animal feeds and as agents for the treatment of mastitis in cattle.

The compounds of formula I may be formulated as oral or parenteral pharmaceutical compositions containing in addition to the active ingredient a pharmaceutically acceptable carrier or diluent. In the treatment of bacterial infections in man, the compounds and compositions may be administered in an amount of from about 5 to 20 mg./Kg./day of active ingredient in divided dosage, e.g. 3 or 4 times a day. They are administered in dosage units containing, e.g. 125, 250 or 500 mg. of active ingredient.

The following examples are given in illustration of, but not in limitation of, the present invention.

DESCRIPTION OF THE PREFERRED EMBODIMENTS

EXAMPLE 1

Disodium 6-[D(−)2-(±)5-Sulfo-2-furyl-5-oxo-4-p-hydroxyphenyl-1-imidazolidinyl]penicillanate

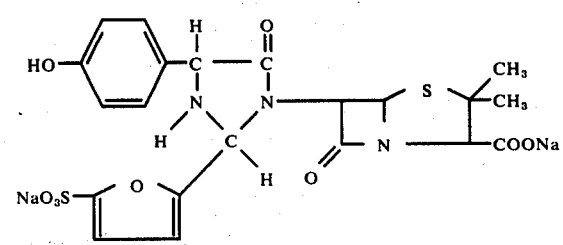

To a mixture of 3 g. (0.015 mole) of sodium 5-formyl-2-furansulfonate in 30 ml. of water at 40°-45° C.

was added with rapid stirring 5 g. (0.014 mole) of amoxicillin trihydrate over a 19 minute period. Separately, a solution of 40% sodium hydroxide was added dropwise to stabilize the solution at pH 7–7.5. The stirring was continued for 15 minutes and the solution was cooled to 20° C. and filtered. The filtrate was lyophilized for 24 hours at 0.1 mm. to yield 7.8 g. of nonhygroscopic product. Bioassay= 696 mcg./mg. (Theory = 730 mcg./mg.). The nmr spectrum (D$_2$O at a concentration of approximately 70 mg./ml.) indicates the presence of 20% of the non-cyclic Schiff's base and 80% cyclic product.

ir (KBr) 1770, 1690–1710, 1590, 1220 cm$^{-1}$ nmr (D$_2$O) δ6.6–7.6 (6H m), 5.9–6.1 (1H d), 5.5–5.7 (1H m), 5.05–5.35 (2H m), 4.7 (DOH,s), 4.05–4.35 (1H m), 1.5–1.7 (6H t)

Anal. Calcd. for C$_{21}$H$_{19}$Na$_2$N$_3$O$_9$S$_2$·2H$_2$O: C, 41.72; H, 3.99; N, 6.95. Found: C, 41.26; H, 3.57; N, 6.74.

As an alternative to the lyophilization recovery method described above, the filtrate may be diluted by addition with rapid stirring to about 600 ml. of isopropanol over a 5 minute period. The resulting precipitate is collected by filtration, washed with 75 ml. of isopropanol and dried in vacuo at 56° C. for 24–48 hours.

The general procedure of Example 1 is repeated with the following changes: (1) Ampicillin trihydrate (3g.) is used in place of amoxicillin trihydrate, (2) 1.6 g. of sodium 5-formyl-2-furansulfonate is used and (3) the reactants are slurried in 15 ml. of water. There is produced the title product as a non-hygroscopic solid. Bioassay = 578 mcg./mg. (Theory = 596 mcg./mg.). The nmr spectrum (D$_2$O at a concentration of approximately 70 mg./ml.) indicates the presence of 20% of the non-cyclic Schiff's base and 80% cyclic product.

ir (KBr) 1770, 1700, 1610, 1220 cm$^{-1}$ nmr (D$_2$O) δ7.4–7.6(5H s), 6.5–7.1 (2H m), 5.9–6.1 (DOH s), 5.0–5.6 (2H m), 4.0–4.35(1H m), 1.3–1.7 (6H t).

Anal. Calcd. for C$_{21}$H$_{19}$Na$_2$O$_8$S$_2$·3H$_2$O; C, 41.65; H, 4.15; N, 6.93. Found: C, 41.10; H, 3.92; N, 6.81.

The product exhibits an in vitro antibacterial spectrum substantially equivalent to that of ampicillin. Oral and intramuscular rat blood levels are substantially equal to those of ampicillin. Paper strip and liquid chromatography indicate that the product is a concentration of 0.2 mg./ml. rapidly hydrolyzes in water (~60–70% hydrolyzed at 0 time by liquid chromatography) to ampicillin in pH 6.5–7.0 buffer or in serum at both room temperature and at 37° C.

TABLE I

| | ANTIBIOTIC ACTIVITY IN NUTRIENT BROTH | | | | |
|---|---|---|---|---|---|
| | | MIC (mcg./ml) | | | |
| Organism | | +Compd of Ex. 1 | Amoxicillin | #Compd of Ex. 2 | Ampicillin |
| Str. pneumoniae* (10$^{-3}$)** | A9585 | .0005 | ≤ .002 | .004 | .008 |
| Str. pyogenes* (10$^{-3}$) | A9604 | .0005 | ≤ .002 | .004 | .008 |
| S. aureus Smith (10$^{-4}$) | A9537 | .06 | .008 | .06 | 0.13 |
| S. aureus +50% serum (10$^{-4}$) | A9537 | 0.13 | .008 | .06 | 0.13 |
| S. aureus bx 1633 (10$^{-3}$) | A9606 | > 125 | > 125 | > 125 | > 125 |
| S. aureus bx 1633 (10$^{-3}$) | A9606 | > 125 | > 125 | > 125 | > 125 |
| S. aureus Meth.-res. (10$^{-3}$) | A15097 | >125 | >125 >125 | 125 | |
| Sal. enteritidis (10$^{-4}$) | A9531 | 0.13 | .008 | 0.013 | 0.013 |
| E. coli Juhl (10$^{-4}$) | A15119 | 1 | 0.5 | 2 | 2 |
| E. coli (10$^{-4}$) | A9675 | 16 | 8 | 16 | 16 |
| K. pneumoniae (10$^{-4}$) | A9977 | 0.13 | ≤ | 0.5 | 0.25 |
| K. pneumoniae (10$^{-4}$) | A15130 | 125 | 125 | 63 | 125 |
| Pr. mirabilis (10$^{-4}$) | A9900 | 0.25 | ≤.016 | 0.13 | 0.25 |
| Pr. morganii (10$^{-4}$) | A15153 | > 125 | 125 | > 125 | 125 |
| Ps. aeruginosa (10$^{-4}$) | A9843A | > 125 | > 125 | > 125 | > 125 |
| Ser. marcescens (10$^{-4}$) | A20019 | 32 | 16 | 32 | 32 |
| Ent. cloacae (10$^{-4}$) | A9656 | > 125 | > 125 | > 125 | > 125 |
| Ent. cloacae (10$^{-4}$) | A9657 | 63 | 63 | 32 | 32 |
| Ent. cloacae (10$^{-4}$) | A9659 | 63 | 125 | 63 | 63 |

*45% AAB + 5% serum + 50% broth
**Dilution of overnight broth culture
+These figures were recirculated on the basis that there was only 60.61% amoxicillin in the sample; in other words, the numerical values were lowered, i.e. improved.
These figures were recalculated on the basis that there was only 53.5% ampicillin in the sample; in other words, the numerical values were lowered, i.e. improved.

The product exhibits an in vitro antibacterial spectrum substantially equivalent to that of amoxicillin. Oral and intramuscular rat blood levels are also substantially equal to those of amoxicillin. Paper strip and liquid chromatography indicate that the product at a concentration of 0.2 mg./ml. rapidly hydrolyzes in water to amoxicillin in pH 6.5–7.0 buffer or in serum at both room temperature and at 37° C.

EXAMPLE 2

Disodium 6-[D(−)2-(±)5-Sulfo-2-furyl-5-oxo-4-phenyl-1-imidazolidinyl]penicillanate

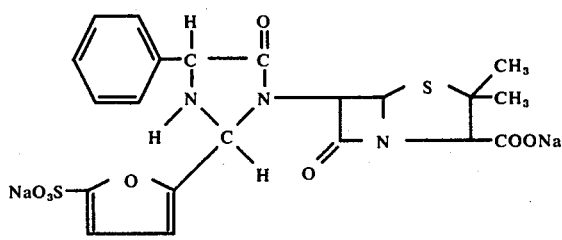

TABLE II

| MOUSE BLOOD LEVELS AFTER INTRAMUSCULAR ADMINISTRATION OF 10 MG./KG. BODY WEIGHT | | | | |
|---|---|---|---|---|
| *Compound | 0.25 | 0.5 | 1 | 1.5 |
| | Hours After Administration | | | |
| Compound of Ex. 1 | 7.3 | 5.4 | 2.1 | 1.1 |
| Amoxicillin | 7.7 | 4.3 | 1.9 | 0.6 |
| Compound of Ex. 2 | 6.3 | 3.7 | 1.3 | 0.6 |
| Ampicillin | 7.8 | 4.5 | 1.5 | 0.6 |

*Each test consisted of six animals and results given are averages of six blood levels. The compounds were dissolved in 0.01% phosphate buffer.

TABLE III

| MOUSE BLOOD LEVELS AFTER ORAL ADMINISTRATION OF 100 MG./KG. BODY WEIGHT | | | | |
|---|---|---|---|---|
| | Blood level | | | |
| *Compound | 0.5 | 1 | 2 | 3.5 |
| | Hours After Administration | | | |
| Compound of Ex. 1 | 6.3 | 7.2 | 3.9 | 1.1 |
| Amoxicillin | 7.9 | 7.4 | 4.6 | 1.5 |
| Compound of Ex. 1 | 9.5 | 10.4 | 4.9 | 1.1 |
| Amoxicillin | 13.9 | 12.4 | 5.8 | 0.8 |
| Compound of Ex. 2 | 1.8 | 2.8 | 1.4 | 0.4 |
| Ampicillin | 4.3 | 4.2 | 1.8 | 0.6 |
| Compound of Ex. 2 | 4.4 | 5.2 | 2.2 | 0.6 |
| Ampicillin | 6 | 4.4 | 2 | 0.6 |

*Each compound was tested twice with 6 mice used in each test. Values given are averages for each test.
The compounds were prepared in Tween-carboxymethylcellulose.

EXAMPLE 3

Potassium Sodium
6-[D(−))2-(±)5-Sulfo-2-furyl-5-oxo-4-p-hydroxyphenyl-1-imidazolidinyl]penicillanate

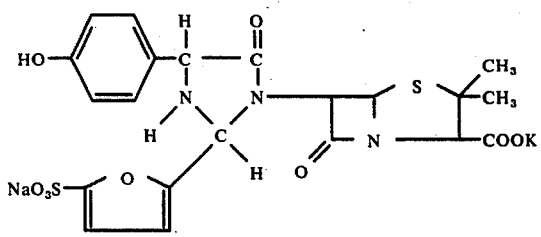

If in the procedure of Example 1 there is substituted 40% potassium hydroxide solution for the sodium hydroxide solution used therein, there is produced the title product.

EXAMPLE 4

Potassium Sodium 6[D(−)2-(±)5-Sulfo-2-furyl-5-oxo 4-phenyl-1-imidazolidinyl]penicillanate

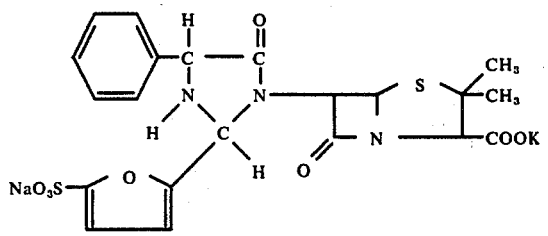

If in the procedure of Example 2 there is substituted 40% potassium hydroxide solution for the sodium hydroxide solution used therein, there is produced the title product.

EXAMPLE 5

Dipotassium
6-[D(−)2-(±)5-Sulfo-2-furyl-5-oxo-4-p-hydroxyphenyl-1-imidazolidinyl]penicillanate

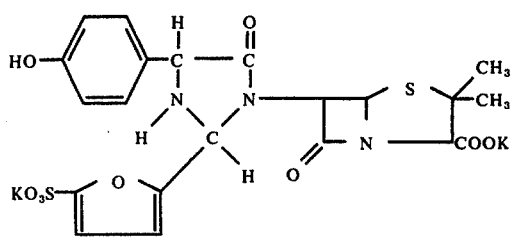

If in the procedure of Example 1 the sodium 5-formyl-2-furansulfonate and 40% NaOH solution are replaced, respectively, by equimolar amounts of potassium 5-formyl-2-furansulfonate and 40% KOH, there is produced the title product.

Use of 40% NaOH instead of 40% KOH in the procedure of Example 5 will give the mixed alkali metal salt.

The potassium 5-formyl-2-furansulfonate used above may be prepared as follows:

Procedure A:

Anhydrous/5-formyl-2-furansulfonic acid (10 g.) is suspended in 350 ml. of water. Potassium hydroxide (2.3 g.; 1 equivalent) is added and the mixture is slurried at 50° C. until solution is obtained. The solution is cooled to 25° C., filtered and the filtrate lyophilized to give the desired product.

Procedure B:

Anhydrous 5-formyl-2-furansulfonic acid (10 g.)) is dissolved in 100–300 ml. of either acetone, methanol, isopropanol, chloroform, methylene chloride or ethyl acetate. To this solution is added with rapid stirring 60 ml. of a 30% weight/volume solution of potassium 2-ethylhexanoate (2 equivalents in acetone or isopropanol whereupon crystals are formed. The reaction mixture is slurried for 10 minutes, filtered and the desired precipitate washed with 100 ml. of acetone and vacuum-dried for 24 hours at 60° C.

EXAMPLE 6

Dipotassium
6-[D(−)2-(±)5-Sulfo-2-furyl-5-oxo-4-phenyl-1imidazolidinyl]penicillanate

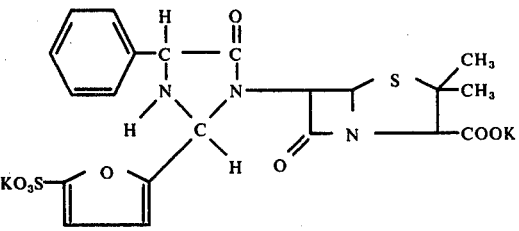

If in the procedure of Example 1 the sodium 5-formyl-2-furansulfonate and 40% NaOH solution are replaced, respectively, by equimolar amounts of potassium 5-formyl-2-furansulfonate and 40% KOH, there is produced the title product.

Use of 40% NaOH instead of 40% KOH in the procedure of Example 6 will give the mixed alkali metal salt.

We claim:

1. A compound having the formula

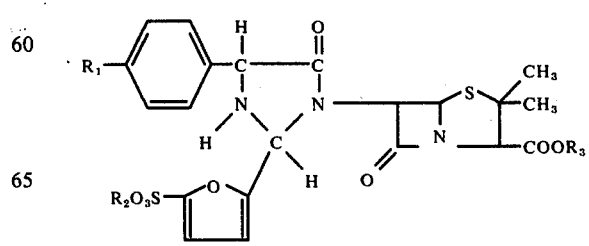

wherein $R_1$ is hydrogen or hydroxyl and $R_2$ and $R_3$ are alike or different and are each sodium or potassium.

2. A compound of claim 1 wherein $R_1$ is hydrogen and $R_2$ and $R_3$ are each sodium.

3. A compound of claim 1 wherein $R_1$ is hydrogen, and $R_2$ and $R_3$ are each potassium.

4. A compound of claim 1 wherein $R_1$ is hydrogen, $R_2$ is sodium and $R_3$ is potassium.

5. A compound of claim 1 wherein $R_1$ is hydroxyl and $R_2$ and $R_3$ are each sodium.

6. A compound of claim 1 wherein $R_1$ is hydroxyl and $R_2$ and $R_3$ are each potassium.

7. A compound of claim 1 wherein $R_1$ is hydroxyl, $R_2$ is sodium and $R_3$ is potassium.

* * * * *